United States Patent
Conley et al.

(10) Patent No.: US 8,897,628 B2
(45) Date of Patent: Nov. 25, 2014

(54) ELECTRONIC VAPORIZER

(76) Inventors: Gregory D. Conley, Medina, OH (US); Daniel C. Hillenbrandt, Medina, OH (US); Michael Mandela, Broadview Heights, OH (US); William E. Steiger, Richfield, OH (US); Rebecca L. Conley, Medina, OH (US)

( * ) Notice: Subject to any disclaimer, the term of this patent is extended or adjusted under 35 U.S.C. 154(b) by 90 days.

(21) Appl. No.: 13/594,813

(22) Filed: Aug. 25, 2012

(65) Prior Publication Data

US 2013/0220315 A1 Aug. 29, 2013

Related U.S. Application Data

(63) Continuation-in-part of application No. 12/843,917, filed on Jul. 27, 2010.

(60) Provisional application No. 61/273,097, filed on Jul. 31, 2009, provisional application No. 61/271,819, filed on Jul. 27, 2009, provisional application No. 61/527,434, filed on Aug. 25, 2011.

(51) Int. Cl.
*A24F 47/00* (2006.01)
*A61M 15/00* (2006.01)
*A01G 13/06* (2006.01)

(52) U.S. Cl.
CPC .................................... *A24F 47/008* (2013.01)
USPC ........................................... 392/386; 392/391

(58) Field of Classification Search
None
See application file for complete search history.

(56) References Cited

U.S. PATENT DOCUMENTS

| | | |
|---|---|---|
| 3,200,819 A | 8/1965 | Gilbert |
| 4,284,089 A | 8/1981 | Ray |
| 4,945,929 A | 8/1990 | Egilmex |
| 4,966,171 A | 10/1990 | Serrano et al. |
| 4,969,476 A | 11/1990 | Bale et al. |
| 5,050,621 A | 9/1991 | Creighton et al. |
| 5,115,820 A | 5/1992 | Hauser et al. |
| 5,249,586 A | 10/1993 | Morgan et al. |
| 5,865,185 A | 2/1999 | Collins et al. |
| 7,412,259 B2 | 8/2008 | Yoo et al. |
| D590,988 S | 4/2009 | Hon |
| D590,989 S | 4/2009 | Hon |
| D590,990 S | 4/2009 | Hon |
| D590,991 S | 4/2009 | Hon |
| D613,903 S | 4/2010 | Wu |
| D613,904 S | 4/2010 | Wu |
| 7,726,320 B2 | 6/2010 | Robinson et al. |
| 7,832,410 B2 | 11/2010 | Hon |

(Continued)

OTHER PUBLICATIONS

Wikipedia; Electronic cigarette—Wikipedia, the free encyclopedia; Feb. 9, 2010; http://web.archive.org/web/20100209122659/http://en.wikipedia.org/wiki/Electronic_cigarette.

*Primary Examiner* — Thor Campbell
(74) *Attorney, Agent, or Firm* — Christopher L. Parmelee; Ralph E. Jocke; Walker & Jocke (57) ABSTRACT

An electronic vaporizer is provided. The electronic vaporizer includes a cartridge that facilitates provision of a vaporized solution to an individual. The cartridge includes a housing that includes an interior, wherein the housing is one of a polymer housing or a ceramic housing. The cartridge also includes a heating element located in the interior of the housing, wherein the heating element is configured to vaporize a solution for oral provision to the individual. The vaporizer may also include a power harvesting device operative to acquire energy from the environment for use with powering the heating element.

21 Claims, 6 Drawing Sheets

(56) References Cited

U.S. PATENT DOCUMENTS

| | | | |
|---|---|---|---|
| 7,832,655 B2* | 11/2010 | Tollens et al. | 239/4 |
| 8,156,944 B2 | 4/2012 | Han | |
| 2005/0016550 A1 | 1/2005 | Katase | |
| 2006/0196518 A1 | 9/2006 | Hon | |
| 2007/0267031 A1 | 11/2007 | Hon | |
| 2008/0073443 A1* | 3/2008 | Tollens et al. | 239/4 |
| 2008/0092912 A1 | 4/2008 | Robinson et al. | |
| 2008/0230052 A1 | 9/2008 | Montaser | |
| 2008/0247892 A1 | 10/2008 | Kawasumi | |
| 2008/0257367 A1 | 10/2008 | Paterno et al. | |
| 2008/0276947 A1 | 11/2008 | Martzel | |
| 2008/0303286 A1* | 12/2008 | Vangel | 290/55 |
| 2009/0095311 A1 | 4/2009 | Han | |
| 2009/0126745 A1 | 5/2009 | Hon | |
| 2009/0272379 A1* | 11/2009 | Thorens et al. | 128/202.21 |
| 2010/0031968 A1 | 2/2010 | Sheikh et al. | |
| 2010/0037903 A1 | 2/2010 | Coleman, III et al. | |
| 2010/0200006 A1 | 8/2010 | Robinson et al. | |
| 2010/0200008 A1 | 8/2010 | Taieb | |
| 2010/0242974 A1 | 9/2010 | Pan | |
| 2011/0011396 A1 | 1/2011 | Fang | |
| 2011/0192399 A1 | 8/2011 | Wilke et al. | |
| 2011/0277757 A1 | 11/2011 | Terry et al. | |
| 2011/0277760 A1 | 11/2011 | Terry et al. | |
| 2013/0309102 A1* | 11/2013 | Gruenbacher et al. | 417/54 |

* cited by examiner

ELECTRONIC VAPORIZER

BACKGROUND

Electronic cigarettes (also referred to as e-cigarettes or personal vaporizers) are generally battery-powered devices that are configured to deliver a vapour that comprises nicotine to an individual. Conventional electronic cigarette designs generally include a battery, a heating element, and a mouthpiece. The mouthpiece includes a liquid solution that comprises nicotine, and the battery provides power to the heating element, which in turn operates to vaporize the solution. Accordingly, when the user places the mouthpiece in her mouth and draws from the mouthpiece, the user receives vaporized nicotine. Due to the ever-increasing taxes on tobacco products, popularity of electronic cigarettes is expected to continue to correspondingly increase.

SUMMARY

The following is a brief summary of subject matter that is described in greater detail herein. This summary is not intended to be limiting as to the scope of the claims.

Described herein are various aspects generally pertaining to electronic vaporizers, and more particularly pertaining to cartridges that comprise heating elements configured to vaporize a solution. In an exemplary embodiment, a cartridge configured for utilization in connection with an electronic vaporizer comprises a housing that has an interior, a first end, and a second end. The housing is constructed of one of a polymer, wood, ceramic or any combination thereof. The cartridge can also include a heating element that resides in the interior of the housing. The cartridge can be manufactured as a single assembly or can be designed so that the cartridge can be manufactured as a multi-piece assembly. The cartridge also comprises a solution that is positioned proximate to the heating element. The heating element is configured to vaporize the solution responsive to receiving power from a power source (e.g., a battery). Pursuant to an example, the cartridge can be designed for utilization as a portion of an electronic cigarette. Accordingly, the solution may comprise nicotine or other components. Furthermore, the solution can be configured such that the vapor has a flavor when received by a user as well as other ingredients.

Additionally, an adapter is described herein, wherein the adapter is configured to electrically or electronically couple a power source (such as a battery) having a first configuration with a heating element having a second configuration. Specifically, manufacturers of vaporizers generally manufacture a power source and a heating element in a proprietary manner, such that only a heating element provided by the manufacturer can be electrically or electronically coupled to a power source provided by the manufacturer. Typically, the power source (battery) is significantly more expensive than associated cartridges, and once a user purchases a power source they may not wish to purchase a different power source from a different manufacturer even if the tastes of the user change over time. The adapters described herein are configured to electrically or electronically couple power sources from a first manufacturer with a heating element from a second manufacturer.

The aforementioned adapter can provide for air flow (both direct and indirect), electrical and or electronic connection, data connections as well as power or an external heating source. The adapter may also incorporate onboard circuitry and/or sensors for collecting data from the adapter.

Other aspects will be appreciated upon reading and understanding the attached figures and description.

DETAILED DESCRIPTION

Various technologies pertaining to electronic vaporizers will now be described with reference to the drawings, where like reference numerals represent like elements throughout. In addition, several functional block diagrams of exemplary electronic vaporizers, cartridges, and/or adapters are illustrated and described herein for purposes of explanation; however, it is to be understood that functionality that is described as being carried out by certain components of the electronic vaporizers may be performed by multiple separate components. Similarly, for instance, a component may be configured to perform functionality that is described as being carried out by multiple components.

Figure 1:
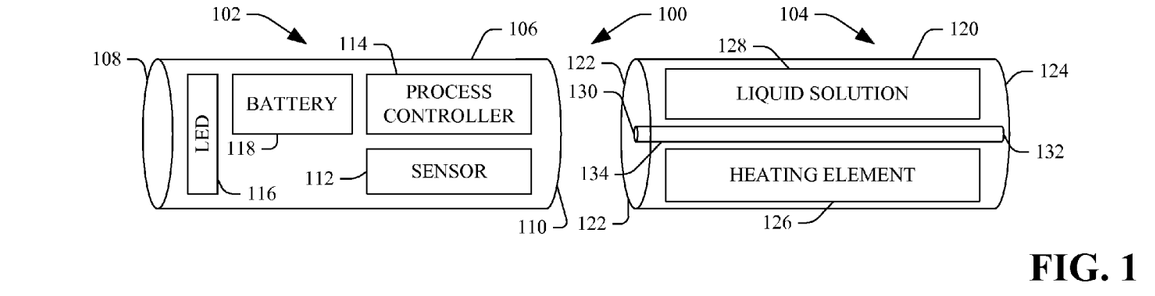
FIG. 1 is a functional block diagram of an exemplary electronic vaporizer.

With reference to FIG. 1, an exemplary electronic vaporizer 100 is illustrated. Pursuant to an example, the electronic vaporizer 100 may be an electronic cigarette that is configured to deliver a vaporized nicotine solution to a user thereof. It is to be understood, however, that the electronic vaporizer 100 may be utilized for other purposes, including deliverance of various vaporized solutions to the user for recreational or medicinal purposes.

The electronic vaporizer 100 comprises a power source 102 and a cartridge 104. The power source 102 and the cartridge 104 are configured to be mechanically and electrically coupled to one another. For example, the cartridge 104 may comprise an electrically conductive threaded fastener, and the power source 102 may comprise an electrically conductive threaded receiver. The threaded fastener and the threaded receiver can be coupled to one another, thereby mechanically and electrically coupling the power source 102 with the cartridge 104. Of course, other types of connection mechanisms that can mechanically and electrically couple the power source 102 with the cartridge 104 are contemplated and are intended to fall under the scope of the hereto-appended claims. These include magnetic connection mechanisms, snaps, twist caps, push on connections, gasketed connections, quick connection mechanisms, turn lock mechanisms, t-bar connections, etc.

The power source 102 comprises a housing 106, which may be manufactured from a metal, a polymer, a ceramic, or some other suitable material. As used herein, a "polymer" can refer to a formulation of manufactured materials comprising plastics, PVC, and/or some other compound that derives from the classification of a polymer or polymer derivative. A "ceramic" refers to a compound that is classified or derivative of such compound that are derived from clay or man-made materials that are listed in a suitable classification scheme as being a ceramic, which may include compounds that are derived with some portion of the compound being ceramic in nature that is a blended or compounded material.

In the example shown and described with respect to FIG. 1, the housing 106 is cylindrical in nature. It is to be understood, however, that the housing 106 may be any suitable shape. As shown, the housing 106 comprises a first end 108 and a second end 110 that is opposite the first end 108, and also includes an interior. While not shown, the second end 110 can comprise an aperture, wherein the aperture is configured to receiver airflow from a user. A switch/sensor 112 resides on the interior of the housing 106. The power source 102 also includes a process controller 114 that is in electrical communication with the switch/sensor 112. The process controller 114, for example, can be a microchip that is configured to cause the power source 102 to operate as desired when the electronic vaporizer 100 is utilized by a user. A light emitting diode (LED) 116 is positioned proximate to the first end 108 of the housing 106. A battery 116 resides in the interior of the housing 106, and is electrically coupled to the LED 116, the process controller 114, and the switch/sensor 112. The process controller 114 controls operation of the LED 116 based at least in part upon output of the switch/sensor 112.

The cartridge 104 comprises a housing 120 that has an interior. The cartridge 104 also comprises a first end 122 and a second end 124, which may be considered as a portion of the housing 120 or apart from the housing 120. The housing 120 of the cartridge is manufactured from a non-metallic material, such as a polymer material or a ceramic material. In an example, the polymer may be a conductive polymer. As shown, the housing 120 is cylindrical in shape. It is to be understood, however, that the housing 120 may be of some other suitable shape. Moreover, the housing 120 may comprise only a cartridge wall (that can be cylindrical as well as other shapes). In another example, the housing 120 may comprise the cylindrical wall and two end-caps, all constructed of the polymer material or the ceramic material. In still yet another embodiment, the housing 120 may comprise the cartridge wall and a single end-cap. One or more end-caps described herein may be constructed from conductive material, such as metal, a conductive polymer, or the like.

A heating element 126 resides in the interior of the housing 120. The heating element 126 may be or include any suitable technology for outputting heat, including resistive heating, laser-based heating, flame, etc. It is to be understood that other technologies can be utilized other than heat to vaporize a liquid solution, including but not limited to ultrasonic technologies, ultraviolet technologies, chemical technologies, etc. Therefore, another state-changing apparatus may be substituted for the heating element 126.

A liquid, gelatin, frozen or solid solution (solution) 128 also resides in the interior of the housing 120, wherein the solution can be suspended in an absorbent material, capsule, or reservoir, wherein such devices may act as the holding medium for the solution 128. The solution 128 may be a mixture that is configured to deliver a particular substance in vaporized form to the user when the solution 128 changes state to a gaseous solution (e.g., subsequent to a sufficient amount of heat being provided to the solution 128). In an example, such substance can be nicotine. In another example, the substance may be tobacco, THC, and/or any derivative thereof. Other substances are also contemplated, such as but not limited to caffeine, vitamins, herbal substances, and any other substance deemed necessary to achieve intended goals, including those that may be desirably delivered to a user for medicinal purposes. In other examples, the substances may include various pharmaceuticals or medications. Thus, as used herein a solution can refer to an element, compound, or substance that is blended, formulated or compounded to be used in the vaporizer 100 in order to deliver the user desired effects and or taste. The solution 128 may be in liquid state, gaseous state, gelatin state, frozen state or solid state.

The first end 122 of the cartridge 104 comprises a first aperture 130 that is located at approximately the center of the first end 122 of the cartridge 104. The second end 124 comprises a second aperture 132 that is located at approximately the center of the second end 124 of the cartridge 104. An airflow passageway 134 extends between the first aperture 130 and the second aperture 132 axially proximate to the center of the housing 120.

In operation, the user mechanically and electrically couples the power source 102 with the cartridge 104. Specifically, the battery 118 is electrically coupled to the heating element 126 when the power source 102 is mechanically coupled to the cartridge 104. The user places the second end 124 of the cartridge 104 in her mouth, and draws air through the airflow passageway 134. The switch/sensor 112 in the power source 106 is configured to detect the drawing of air through the airflow passageway 134, and an electric circuit is closed between the battery 118 and the heating element 126. The process controller 114 controls an amount of voltage/current to be received by the heating element 126 from the battery 118, such that the heating element 126 receives an appropriate amount of electrical current/voltage. The heating element 126 outputs a sufficient amount of heat to vaporize at least a portion of the solution 128, and the user receives the vaporized solution orally. When the user ceases to draw air by way of the air passageway 134, the sensor/switch 112 detects the lack of airflow in the air passageway 134, and the electric circuit between the battery 118 and the heating element 126 is opened (e.g., directly by the sensor/switch 112 or responsive to receipt of instructions from the process controller 114) with or without delay circuitry built into the control. Manual switching or activation of the power source is also an option.

With respect to the power source 102, the battery 118 may be any suitable disposable, replaceable and/or rechargeable battery, including but not limited to a alkaline, lead acid battery, gel, a nickel cadmium battery, a nickel metal hydride battery, a lithium ion battery, a lithium ion polymer battery, amongst others. Other power sources may also be used in place of a battery such as direct power from any DC, AC or alternative energy source including inductive, solar, chemical, perpetual motion, etc. that can be used to power a heating source. Indirect or direct flame may also be used as a power source as appropriate to trigger the state change of the solution 128 from an initial state to a gaseous aerosol state. As mentioned previously, the process controller 114 can be a microchip or microcontroller that operates as desired when used (or not used) by an individual in regards to the electronic vaporizer 100. Thus, the process controller 114 can receive readings from the switch/sensor 112, and can cause the voltage/current to be supplied to the heating element 126 in the cartridge 104 as a function of such readings. The switch/sensor 112 can be a switch, a sensor, or a combination of a switch and sensor. For instance, the switch/sensor 112 may comprise an electronic airflow sensor, wherein the electronic airflow sensor senses when the user is drawing on the electronic cigarette 100. Additionally or alternatively, the switch/ sensor 112 may comprise a tactile sensor that is configured to sense that the user has depressed a tactile button on the cartridge 104 and/or the power source 102. That is, the user depresses a button to activate the heating element and draw the vaporized solution from the electronic vaporizer 100. Still further, the switch/sensor 112 may comprise a timed switch that opens the circuit between the battery 118 and the heating element 126 after the circuit has been closed for a threshold amount of time. There are a variety of switches and sensor that can be used to detect air flow and/or pressure that can be utilized to activate the heating element.

With respect to the cartridge 104, as mentioned previously, the main body of the housing 120 is constructed of a polymer. The first end 122 and the second end 124 may be or include end caps, wherein such end caps may be constructed of the polymer. In an exemplary embodiment, an end cap coupled to the first end 122 may at least be partially constructed of a conductive material, such as a conductive metal or a conductive polymer. Furthermore, a wood tip may be positioned upon the second end 124, wherein the wood tip is configured to be received orally by the user. In alternative embodiments, the second end 124 may include a tip comprised of a soft, malleable and/or a flexible polymer. Also in alternative embodiments, the second end 124 may include a paper wrapping around the tip of the second end in order to more closely simulate the tip of a conventional cigarette. Such a paper wrapping may further include flavorings capable of being tasted by a user (e.g., mint, tobacco, candy, fruit, or any other types of flavorings and/or aromas).

Additionally, as described above, the solution 128 may be placed in an absorbent material, such as cotton, wool, polyester, a batting material, or some other suitable absorbent material. A wicking material may be used in order to channel the liquid or gel to the heating element. Pursuant to an example, the solution 128 may include a primary substance, such as propylene glycol, glycerin (both vegetable and man-made), glycerol and/or any combination thereof. Additionally, the solution 128 may comprise a portion of amount of a particular drug, such as nicotine, caffeine, THC, other stimulants or medicinal substance. Further, the solution 128 may comprise some amount of flavoring, such as tobacco flavoring, menthol flavoring, other suitable flavoring or any combination thereof.

Figure 2:
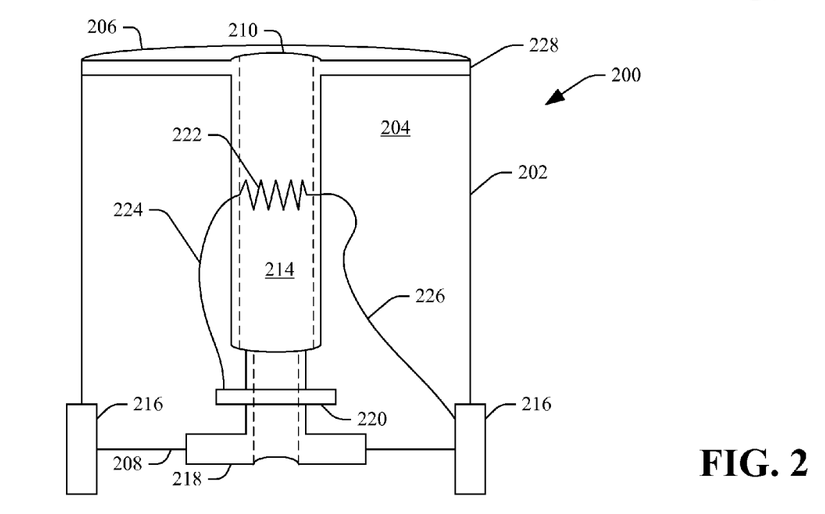
FIG. 2 is an exemplary configuration of a cartridge for utilization in an electronic vaporizer.

Now turning to FIG. 2, a cutaway diagram of an exemplary cartridge 200 for utilization in an electronic personal vaporizer is illustrated. The cartridge 200 comprises a housing 202, which is constructed of a non-metallic material, such as a polymer, wood, ceramic, and/or any combination thereof. The housing 202 comprises an absorbent material 204 that has a liquid solution absorbed therein in a measured dose. The cartridge 200 includes a first end 206 and a second end 208 that is opposite the first end 206, wherein the first and second ends 206 and 208 can be removable caps, respectively. In an example, the first end 206 is formed of a polymer, and the second end 208 is formed of a conductive material, such as a conductive polymer or a conductive metal.

The first end 206 comprises a first aperture 210, and the second end 208 comprises a second aperture 212. As shown, the first aperture 210 and the second aperture 212 are positioned at approximately the centers of the first and second ends 206 and 208, respectively, such that a central axis of the cartridge 200 passes through both apertures 210 and 212. Both or either the first end 206 or second end 208 can be integrated into a single assembly as part of the housing 202. Additionally, the resulting assembly may or may not be able to be unassembled by the end user. An air passageway 214 begins at the first aperture 210 and extends to the second aperture 212 approximately along the central axis of the cartridge 200. For example, the wall of the air passageway 214 may be constructed from a polymer or other suitable material.

The cartridge 200 further comprises a conductive element 216, at least a portion of which resides in the interior of the housing 202. For instance, the conductive element may be metallic threads that facilitate mechanically and electrically coupling the cartridge 200 with a power source (battery). The cartridge further comprises a center post 218 that extends from the second end 208 of the cartridge 202 to the airflow passageway 214, wherein the center post 218 is hollow to allow the airflow passageway 214 to extend through the center post 218 to the second aperture 212. In an example, the center post 218 can be formed of a conductive material, and may be constructed as being a portion of an end cap. An electrical isolator 220 is coupled to the center post 218 and extends outward from the center post 218. For instance, the electrical isolator 220 may be an O-ring or other suitable isolator.

The cartridge 200 further comprises a heating element 222 that is coupled to the electrical isolator 220 and the conductive element 216 in the interior of the housing 202 by way of conductive lines 224 and 226. The heating element 222 can comprise wicking material that draws the liquid solution from the absorbent material 204 towards the heating element 222. When the cartridge 200 is coupled to a power source, the conductive element 216 is electrically coupled to a negative terminal of the power source and the center post 218 (and thus the electrical isolator 220) is electrically coupled to a positive terminal of the power source. When a user draws a breath by way of the airflow passageway 214, a circuit is closed, thereby providing current to the heating element 222. The heating element 222 acts to vaporize the liquid solution in the absorbent material 204, and the resulting vapor is received by the user. Additionally, as shown, a gap 228 may exist between the first end 206 of the cartridge 200 and the absorbent material 204. This gap 228 can be utilized to mix air and the vaporized liquid solution to provide the user with an appropriate amount of vaporized solution.

While the heating element 222 is shown as residing solely in the airflow passageway 214, it is to be understood that various other configurations of the heating element 222 with respect to the airflow passageway are contemplated and are intended to fall under the scope of the hereto-appended claims. In a first example, the heating element 222 may reside on the exterior of the airflow passageway 214, such that the heating element 222 heats the airflow passageway 214 by heating the wall of the airflow passageway 214. In a second example, the heating element 222 may reside on the interior and the exterior of the airflow passageway 214. In yet another example, as will be shown in greater detail below, the heating element 222 can be helical in nature and may wrap around the airflow passageway 214, which may be constructed of a ceramic. In such a design, the wall of the airflow passageway 214 may have apertures, be permeable, or be conductive to heat such that the vaporized liquid solution may be provided to the user. Furthermore, the airflow passageway 214 itself may act as a heating element, wherein the airflow passageway 214 is constructed from an electrically conductive and a thermally conductive material, such as a conductive ceramic. Accordingly, it is readily recognized that airflow may pass directly over the heating element, through a chamber that is proximate to the heating element, or other suitable configuration.

It is to be understood that the cartridge design shown in FIG. 2 is merely but one example of a cartridge design, and numerous other designs that cause a heating element to reside in a non-metallic housing together with a liquid solution that is desirably vaporized are contemplated.

Also, an alternative embodiment of a cartridge (adapted to mount to the described power source) may be configured to receive one or more capsules or pellets. Such capsules or pellets may be comprised of one or more medicines, vitamins, a tobacco, and/or other chemical(s) that the end user may desire to taste/consume. In such an embodiment, when the cartridge with a capsules is mounted to a power source (e.g. such as the power source 104 discussed above), the mechanical connection of the cartridge and power source may cause the capsule to open and release the contents therein. The end user may then provide a suction on the tip of the cartridge with his/her mouth in order to draw the released contents of the capsule into his/her mouth. In examples of this described embodiment, the capsule may be included in the cartridge during the manufacturing of the cartridge. However, it should be appreciated that in other embodiments, the cartridge may be designed to accept one or more capsule therein via a pharmacist and/or an end user prior to mounting the cartridge to a power source. Also it should be appreciated that this described example of the cartridge may also include a heating element therein that is configured to heat a capsule (or a pellet) to cause release of the contents of the capsule/pellet when the cartridge is mounted to the power source or when other actions are detected (e.g. a button press, suction through the cartridge).

Figure 3:
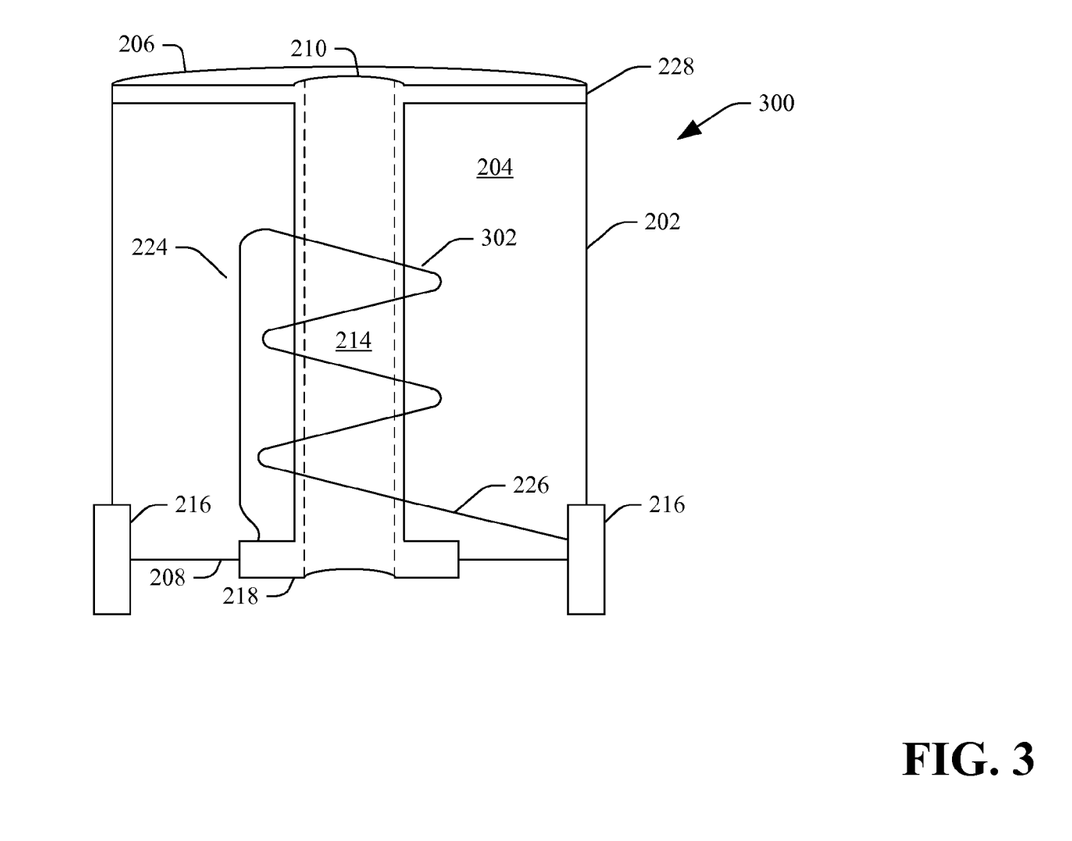
FIG. 3 is an exemplary configuration of a cartridge for utilization in an electronic vaporizer.

Referring now to FIG. 3, another cutaway diagram of an exemplary cartridge 300 for utilization in an electronic personal vaporizer is illustrated. In this exemplary cartridge 300, the center post 218 may be of a conductive material, such as a conductive ceramic or a metallic material, and may act as a heating element. Thus, walls of the airflow passageway 214 may become heated when a user draws on the cartridge, thereby altering the state of the liquid solution in the absorbent material 204 to a vapor for provision to the user. Similar to the previously described exemplary cartridge 200 (FIG. 2), the gap 228 may exist to facilitate mixing of vaporized solution with air. This gap is optional, as other designs may call for the walls of the airflow passageway 214 to be permeable or have apertures therein, to allow for vaporized solution to mix with air in the airflow passageway 214.

In another exemplary embodiment, a heating element 302 may be helical in nature and may wrap around the exterior of the airflow chamber 214. The heating element in this case may also be an integrated material as part of the airflow chamber. The air flow chamber in all cases may be solid or porous in nature or have ventilation to allow for aerosol and air stream blending. The walls of the airflow chamber may be constructed of a thermally conductive material, such as a ceramic, which causes the walls of the heating element to generate a sufficient amount of heat to vaporize the liquid solution in the absorbent material 204. In such a design, the conductive lines 224 and 226 may be coupled to the center post 218 and the conductive element 216, respectively, thereby electrically coupling the heating element 302 to negative and positive terminals of a power source. When the user draws on the cartridge, current is provided to the heating element 302 by way of the conductive lines 224 and 226 from the power source. The heating element 302 then heats the walls of the airflow passageway 214 to a temperature that is sufficient to alter the state of the liquid solution in the absorbent material 204 when the user draws on the cartridge 300. Again, these designs are merely exemplary in nature, and various other designs are contemplated by the inventors and are intended to fall under the scope of the hereto-appended claims.

Figure 4:
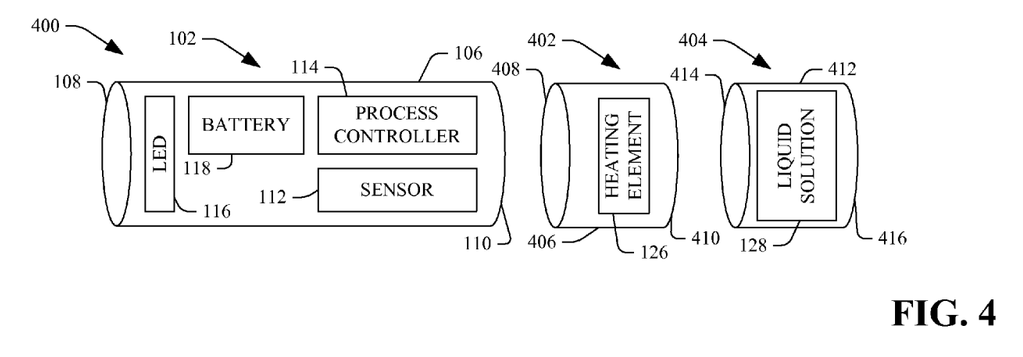
FIG. 4 is a functional block diagram of an exemplary electronic vaporizer.

With reference now to FIG. 4, another exemplary electronic vaporizer 400 is illustrated. The exemplary electronic vaporizer 400 comprises three separate portions: 1) the power source 102; 2) a first cartridge 402 that comprises the heating element 126; and 3) a second cartridge 404 (a mouthpiece cartridge) that comprises the solution 128. Operation of the power source 102 has been described above, and is not repeated here for sake of brevity.

The first cartridge 402 can comprise a housing 406 that is cylindrical in nature, wherein the housing 406 can be constructed from a non-metallic material such as a polymer or ceramic. The housing 406, of course, may be manufactured to be in a shape other than a cylinder. The first cartridge 402 includes a first end 408 and a second end 410 that is opposite the first end 408. The first end 408 of the first cartridge 402 is configured to be mechanically coupled to the second end 110 of the first cartridge 402. Mechanical coupling of the power source 102 and the first cartridge 402 causes the battery 118 to be electrically coupled to the heating element 126 as described above. The heating element 126 can be positioned proximate to the second end 310 of the first cartridge 402, and thus proximate to the solution 128 in the second cartridge 404.

The second cartridge 404 comprises a housing 412, wherein the housing 412 can be constructed of a pliable plastic material. The second cartridge 404 can comprise a first end 414 and a second end 416 that is opposite the first end 414, wherein the first end 414 is configured to be mated with the second end 410 of the first cartridge 402, and the second end 414 is configured to be received orally by a user. The first cartridge 402 and the second cartridge 404 may have airflow passageways (not shown) extending axially there through, such that the switch/sensor 112 can determine when the user is drawing air through the airflow passageways. The process controller 114 can cause an appropriate current/voltage to be provided to the heating element 126 by way of the battery 118, and the heating element 126 can vaporize the solution 128 in the third cartridge 404, thus providing the user with a vaporized substance.

While the designs of the electronic vaporizer described above include an internal direct heating element, it is to be understood that alternative designs are contemplated, wherein the heating element is reusable or disposable and is located exterior to the housing. In such a design, the heating element transfers heat to the solution in order to vaporize the solution for oral provision to a user.

Figure 5:
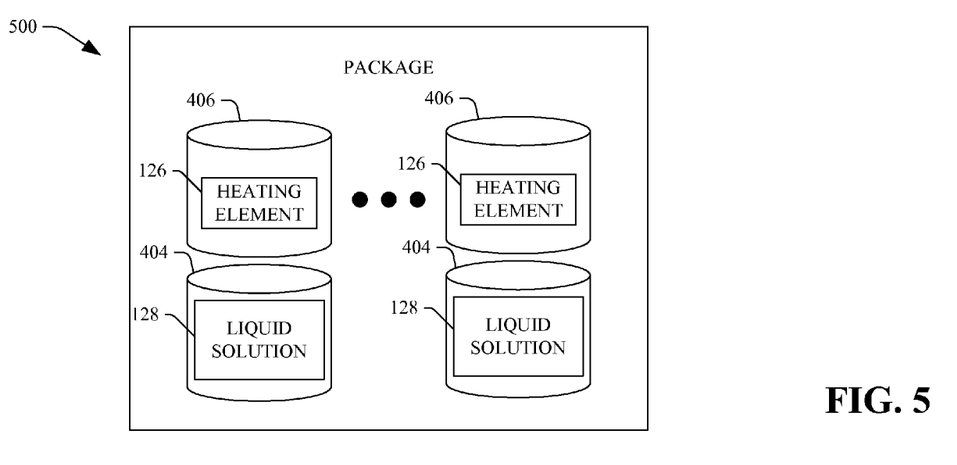
FIG. 5 is a functional block diagram of an exemplary package of cartridges.

Referring now to FIG. 5, an exemplary package 500 is illustrated, wherein the package 500 is configured for sale to consumers. The package 500 comprises a plurality of first cartridges 402 and a corresponding plurality of second cartridges 404, which have been described in detail above with respect to FIG. 4. The package 500 may be a tamper-proof package, with each combination of first and second cartridges sharing a compartment in the package 500.

Figure 6:
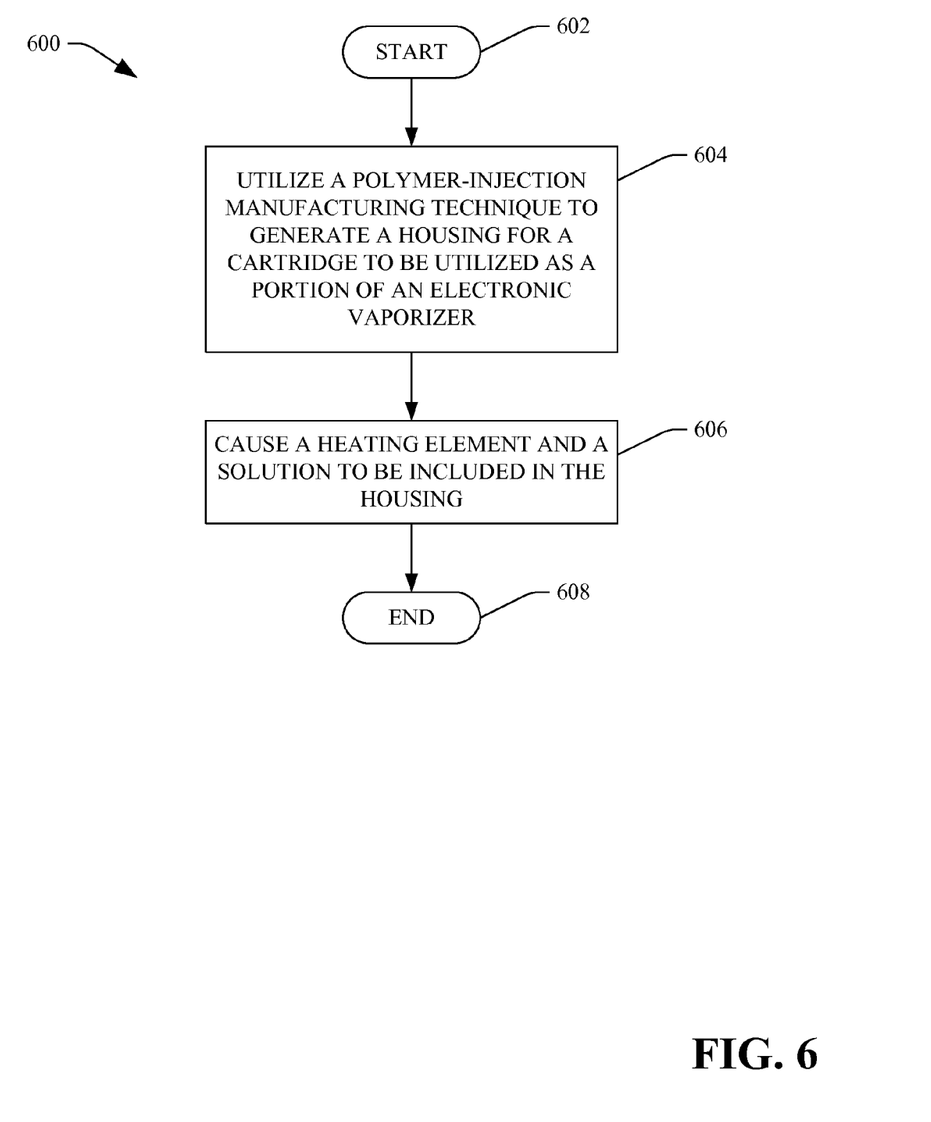
FIG. 6 is a flow diagram illustrating an exemplary methodology for manufacturing a cartridge for employment in an electronic vaporizer.

With reference now to FIG. 6, an exemplary methodology is illustrated and described. While the methodology is described as being a series of acts that are performed in a sequence, it is to be understood that the methodology is not limited by the order of the sequence. For instance, some acts may occur in a different order than what is described herein. In addition, an act may occur concurrently with another act. Furthermore, in some instances, not all acts may be required to implement a methodology described herein.

With more specificity pertaining to FIG. 6, a methodology 600 that facilitates constructing a cartridge for utilization in connection with an electronic vaporizer is illustrated. The methodology 600 begins at 602, and at 604 a polymer-injection manufacturing technique is utilized to generate a housing for the cartridge. The polymer-injection manufacturing technique may be a multi-step polymer injection. Other manufacturing techniques are also contemplated (but not limited to), including chemical bonding, thermal molding, thermal bonding, molding through utilization of metal molds, form casting, roll forming, machining, amongst others.

At 606, a heating element and liquid solution (e.g., placed in an absorbent material) are caused to be included in the housing. For instance, the housing can be cylindrical in nature with a size approximately the size of a filter on a cigarette. The heating element and the liquid solution reside in the interior of the housing. The methodology 600 completes at 608.

Figure 7:
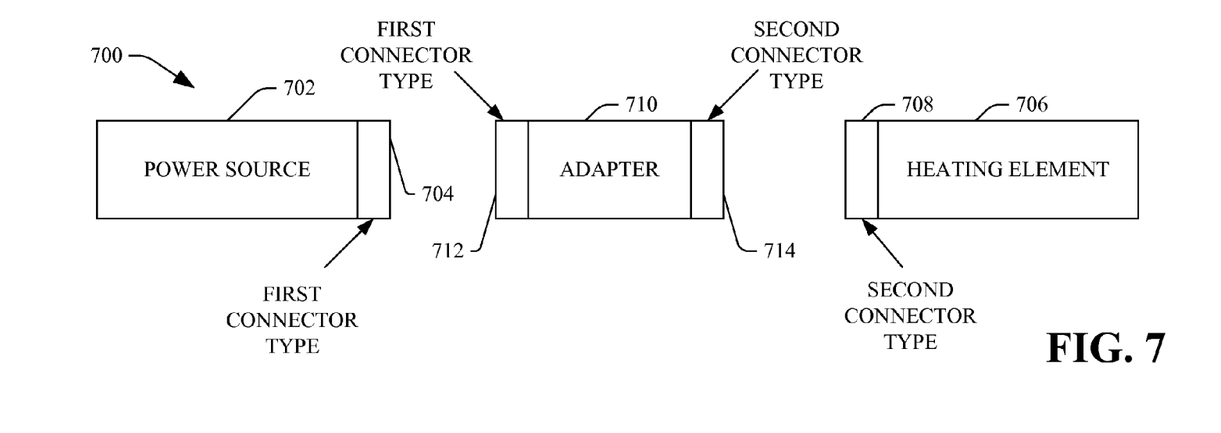
FIG. 7 is a functional block diagram of an exemplary adaptor.

Turning now to FIG. 7, an exemplary personal electronic vaporizer 700 is illustrated. In a first embodiment, the electronic vaporizer 700 may be an electronic cigarette. In another embodiment, the electronic vaporizer 700 may be a drug delivery device for utilization in a medical field. The electronic vaporizer 700 comprises a power source 702 that is of a particular type. For example, the power source 702 may be manufactured by a particular manufacturer. In another example, the power source 702 may be a particular model of power source. Accordingly, the power source 702 has a connector 704 corresponding thereto that is of a first type that is associated with the particular type of the power source 702. Pursuant to an example, the power source 702 may be a battery that is commonly utilized in electronic cigarettes. In another example, the power source 702 may be an automobile battery, a AA battery, a portable telephone, a 9 volt battery, a personal computer, an AC outlet, a generator, or some other suitable power source.

The electronic vaporizer 700 also comprises a heating element 706 that is of a type that is different than the type associated with the power source 702. For example, the heating element 706 may be manufactured by a manufacturer that is different from the manufacturer of the power source 702. Thus, the heating element 706 can have a connector 708 that is of a second type that is different than the type of the connector 704 on the power source 702. Pursuant to an example, the first connector type may be a threaded connector, a magnetic connector, a push-on connector, a snap-on connector, a turn-lock connector, or other suitable connector type. The second connector type may be some connector type that is different from the first connector type.

The electronic vaporizer 700 also comprises an adapter 710 that is configured to mechanically mate the power source 702 with the heating element 706 by way of the adapter 710. Additionally, the adapter 710 is configured to electrically couple the power source 702 with the heating element 706. Thus, the adapter 710 comprises a first connector 712 that is of the first type (the same type as the connector 704 of the power source 702) and a second connector 714 that is of the second type (the same type as the connector 708 of the heating element 706). In an example, if the connector 704 is a threaded connector, the first connector 712 on the adapter 710 may be a threaded connector that is configured to receive or screw into the connector 704 of the power source 702. Additionally, while not shown, the adapter 710 may comprise an airflow passageway that allows airflow to reach the power source 702 when a user draws on the electronic vaporizer 700. Accordingly, the adapter 700 may be at least partially constructed of a conductive material, such as a conductive metal or a conductive polymer.

Figure 8:
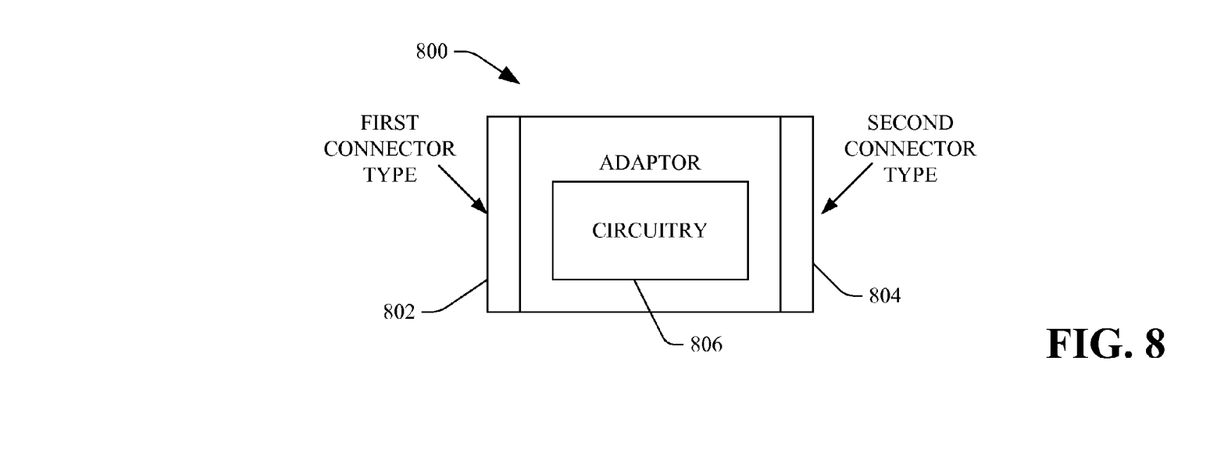
FIG. 8 is a functional block diagram of an exemplary adaptor.

With reference now to FIG. 8, an exemplary adapter 800 that facilitates mechanically mating and electronically coupling a power source and a heating element in an electronic vaporizer having dissimilar connection mechanisms is illustrated. The adapter 800 comprises a first connector 802 of a first type and a second connector 804 of a second type. The first connector 802 is configured to mechanically and electrically mate with a power source and the second connector 804 is configured to mechanically and electrically mate with a heating element. Accordingly, the power source is electrically and mechanically coupled to the heating element by way of the adapter 800.

The adapter 800 also comprises circuitry 806, which can be or include microchip, a voltage regulator, an AC/DC converter, an amplifier, circuitry that is configured to step up or step down voltage received from the power source, or some other suitable circuitry that can allow for power delivered from the power source to properly operate the heating element to cause vapor to be provided to a user as desired. Accordingly, while not shown, the adapter 800 can comprise an airflow passageway that allows air to flow between the heating element and the power source by way of the adapter.

As mentioned previously, the connectors 804 and 806 may be of dissimilar type. Therefore, for instance, the first connector 804 may be one of a threaded fastener, a magnetic connector, a twist cap connector, a push-on connector, a quick-lock connector, a t-bar connector, a half-turn lock, amongst other type of connectors, and the second connector 806 may be of a type that is dissimilar from the type of the first connector 804.

Figure 9:
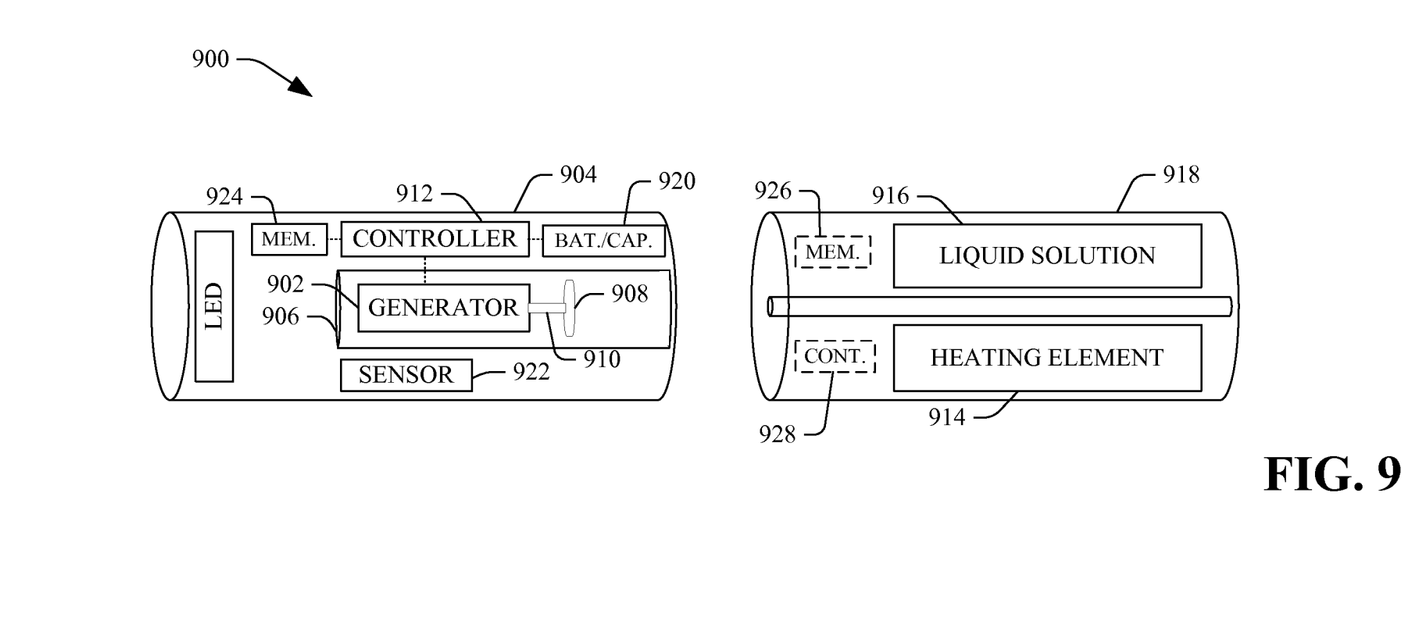
FIG. 9 is a functional block diagram of an exemplary electronic vaporizer that includes a power harvesting device.

As discussed previously with respect to FIG. 7, an example embodiment of a personal electronic vaporizer may include a power source 702 that corresponds to a generator. Such a generator may correspond to a power harvesting device operative to generate electricity from energy in the environment associated with the personal electronic vaporizer. FIG. 9 shows an example 900 of a personal electronic vaporizer that includes a power harvesting device such as a generator 902 as the power source. In this example, the generator 902 is mounted in a housing 904 of the electronic vaporizer. The housing 904 also includes an airflow passageway 906 that extends adjacent at least portions of the generator.

The generator may include at least one actuator device 908 such as an blade, impeller, fan, turbine, propellerairfoil, squirrel-cage impeller, electron mass inductor, plasma accelerator and/or other type of device that is responsive to airflow through the airflow passageway 906 to urge a shaft 910 of the generator to rotate and generate an electrical current. There may also be a venturi, airduct, air ram or other channelling and/or funnelling technologies used in order to increase or decrease the speed and/or volume of the airflow. The generated electrical current may be directed via a controller 912 (e.g., a microprocessor and/or analog circuitry) included in the electronic vaporizer to power a heating element 914 sufficiently to vaporize a portion of a liquid solution 916. As described in previous embodiments, the heating element 914 and the liquid solution 916 may be integrated into a second housing 918 that is adapted to removably connect to the first housing 904.

As can be appreciated, the amount of electrical energy generated by the generator 902 will vary depending on the amount of air drawn through the airflow passageway 906 by a user inhaling and/or exhaling through the electronic vaporizer. In an example embodiment, the controller may be capable of regulating electricity generated from one or more inhales/exhales through the airflow passageway in order to provide the heating element with sufficient power to vaporize a portion of the liquid solution 916. For example, the controller 912 may be in operative connection with a storage device 920 such as one or more capacitors and/or a battery. Electrical energy generated by the generator from several inhales/exhales through the airflow passageways may be stored in the storage device 920. When a sufficient amount of energy is accumulated, the controller 912 may be operative to direct power to the heating element from the storage device in order to vaporize the liquid solution.

In order to ensure that the heating element is activated at a time desirable by a user, power to the heating element may be triggered by the controller responsive to information available to the controller (such as an air flow indication provided by a dedicated airflow sensor). However, rather than using a dedicated air flow sensor, in some embodiments, electricity generated from the generator itself may instead serve as a sensor indicating when a user is actively inhaling through the electronic vaporizer. The detection of inhaling coupled with a detection of a sufficient amount of energy in the storage device may cause the controller to power the heating element.

However, it should be appreciated that in other embodiments, additional or other information may be used to trigger the power of the heating element. For example, wind or other external air source may also be operative to urge the actuator device to turn the shaft of the generator. In order to prevent wind from activating the heating element at undesirable times, the electronic vaporizer may include at least one further sensor 922 adapted to sense that a user is holding and/or is ready for the electronic vaporizer to operate. Such a further sensor may correspond to a button or a switch, which is activated in order for the heating element to be powered.

In this described embodiment, the generator corresponds to a power harvesting device operative to acquire energy from airflows. However, it should be appreciated that in alternative embodiments of the electronic vaporizer, other types of power harvesting devices may be used. For example, an embodiment may include an induction device operative to acquire electrical power for charging a battery wirelessly via induction from an induction source near the electronic vaporizer. In another example, the power harvesting device may correspond to an inductive jet that is operative to generate electricity responsive to airflow through the inductive jet, venturi or any other mechanism that directs a air or gas flow (including air) that could or may increase or decrease the gas speed and/or volume. Furthermore this may be used as an induction system pulling gases or vapors from a secondary stream for more flow mass/speed or to use as a mixing and/or blending mechanism.

In further embodiments, the electronic vaporize may include a power harvesting device in the form of a radio frequency (RF) power receiver device that is operative to acquire electrical power from RF signals transmitted by an RF power transmitter device. In further embodiments, the power receiver may be operative to harvest power from other RF sources in the environment such as wireless network signals and/or mobile phone communication signals. Examples of RF power harvesting devices include the Powerharvester modules sold by Powercast Corporation in Pittsburgh, Pa.

Also, in further example embodiments, the electronic vaporizer may include a power harvesting device in the form of a vibration power receiver which is operative to convert mechanical vibrations (e.g., accelerations caused by movement of the electronic vaporizer) to electrical energy. Power harvesting devices may also include solar cells, static electricity harvesters, or any other type of device capable of harvesting power from energy sources in the vicinity of the detection device.

In these described embodiments, the power harvesting device may be operative to charge a rechargeable battery with the acquired electrical energy. The other components of the electronic vaporizer (e.g., the controller and heating element) may be powered via the battery. However, it is to be understood that example embodiments of some of the described harvesting devices may directly provide power to the controller and heating element without using a battery.

In example embodiments that include a generator, the controller may be operative to estimate an amount of airflow being drawn through the airflow passageway responsive to the electrical output from the generator. The controller may also be operative to determine when such an air flow includes a vaporized solution caused by the powering of the heating element by the controller. With such information, an example embodiment of the controller may be operative to estimate an amount of the vaporized solution that is likely being inhaled by the user. The controller may be operative to use this information to regulate and control the dosage of the vaporized solution received by the user. In this embodiment, the electronic vaporizer may correspond to a metered dosage inhaler (MDI) for nicotine, medications (e.g., for treatment of an asthma attack or other condition), and/or other chemicals.

For example, as illustrated in FIG. 9, the controller may include a data store 924 such as a flash memory device or other non-volatile memory in which the controller is operative to store information regarding the amounts of vaporized solution that a user may have inhaled. The controller may also be operative to store time and/or date information in association with the measured amounts of inhaled vaporized solution. An example embodiment of the controller may be operative to operate the heating element responsive to the information stored in the data store. The controller may be operative to limit the amount of the vaporized solution that a user is able to inhale over a given predetermined (and/or configurable) period of time. This may be accomplished by the controller monitoring the amount of vaporized solution that is likely inhaled via the device for a predetermined period of time. When the monitored amount reaches a predetermined threshold, the controller may be operative to prevent the heater element from vaporizing additional solution, until after a predetermined amount of time, and/or until after the controller receives a manual reset signal (via a button, or other sensor device) included in the electronic vaporizer. These described predetermined periods of time and predetermined thresholds may be stored in the data 924.

In one or more of the previously described embodiments (e.g., embodiments with either a battery or a power harvesting device), the described controller 912 (and/or a controller 928 in the housing 918 with the solution 916) may be operative to prevent the heater element from operating to vaporize a solution unless a specific user is detected by the electronic vaporizer. For example, in cases where the solution includes a prescription medication, a pain killer, a pharmaceutical, a narcotic, a controlled substance and/or other chemical, which is intended to be used by a specific person, the electronic vaporizer may include a sensor (e.g., such as sensor 922 in FIG. 9) that corresponds to a fingerprint reader or other type of biometric device. Such a biometric device may acquire data from a user which is used by the controller 912 and/or 926 to verify that a predetermined user is currently holding the electronic vaporizer prior to vaporizing the solution.

In this described embodiment (with reference to FIG. 9), a further data store 926 (e.g., a non volatile memory) may be included in the particular housing 918 that holds the solution (e.g., a prescription medication). This further data store 926 and/or data store 924 may be programmed (e.g., via a pharmacist) to include the biometric data associated with the user being treated with the prescription medication). The biometric data couples one or both of the housings 904, 918 to a particular user. Prior to causing the heater element to vaporize the solution with the prescription medication, the controller 912 and/or 928 may require the coupled user to provide (through a sensor 922) a biometric input that corresponds to the biometric data programmed into the data store 924 and/or 926.

In another example, the electronic vaporizer may be capable of having a data store be programmed (with the biometric data) by the owner of the device. In this embodiment, the electronic vaporizer may include one or more input devices through which the data store 924 or 926 can be updated with biometric data usable to couple the vaporizer to a specific user. Also, in an embodiment, the electronic vaporizer may include a communication device (e.g. a USB port, Bluetooth, Wireless Ethernet) capable of connecting to an external computing device (PC, mobile phone, or other computing device) through a wired or wireless connection. The external computing device may be operative to execute software capable of updating the data store 924 or 926 in the electronic vaporizer to included biometric data that couples the device to a specific user. Coupling an electronic vaporizer to a particular user may minimize the opportunity for children or other people from using the electronic vaporizer without permission.

It should also be appreciated that further embodiments may include other features for coupling an electronic vaporizer to a particular user. For example, the sensor 922 may correspond to an RFID, Bluetooth, and/or NFC reader that is operative to wirelessly read an RFID chip or other circuit (Bluetooth, NFC) integrated into an article associated with the user. Such an RFID chip or other circuit may be integrated into an article such as a ring, bracelet, necklace, card, mobile phone, clothing, or other article worn and/or carried by the user. The RFID chip or other circuit may include a unique code that corresponds to data stored in the data store 924 and/or 926. The controller 912 and/or, 928 may be operative to verify that the data stored in the data store 924 and/or 926 corresponds to code recently or currently being read by the RFID reader or other reader from the RFID chip or other circuit of the user's article, before causing the heater element to vaporize the solution. As described previously with respect to the embodiment with biometric data, a pharmacist and/or an end user may include computing devices capable of interfacing with one or both controllers 912, 928 and storing data associated with the user's article in the data store 926 and/or 924.

To enhance security and to minimize unauthorized access to the electronic vaporizer or housings included therein, read only memory may be used as a data store for storing serial numbers, public keys, or other data that is intended to remain constant. Furthermore, updateable data (e.g. biometric data, RFID/Bluetooth/NFC data) which are programmed into a data store 924 and/or 926 by a pharmacist or other authorized person (to carry out the previously described data couplings), may be digitally signed in a manner that can be authenticated by one or more of the controllers 912, 928 in the electronic vaporizer prior to allowing the heater element to vaporize the solution.

For example, data stored in a data store 924 and/or 926 that couples the electronic vaporizer to a particular RFID chip or other circuit enabled article (e.g. a ring) may correspond to a digitally signed certificate that specifies the code that is transmitted by the article. Prior to enabling the heater element to vaporize the liquid solution, at least one of the controllers 912, 928 may require the detection of a code from an article which matches the code stored in the certificate, as well as requiring that the signature of the certificate be cryptographically authenticated. Further, the controller 912 and/or 928 may verify that the certificate includes serial number(s) associated with one or more of the housings 904, 918.

Such validly signed certificates may only be generated and stored on the electronic vaporizer by a pharmacists or other person that has access to a server with the particular private key that can sign the certificate in a manner that can be authenticated using the public key securely stored in the electronic vaporizer. Thus, an unauthorized user would not be able to reprogram the electronic vaporizer (or the housing 918 that contains the solution 916) to work with other RFID articles by installing a fake certificate in the data store 924 and/or 926.

In addition, it should also be understood that in some embodiments a handshaking protocol may take place between controllers in different housings of the electronic vaporize to establish encrypted communications. Such encrypted communications may minimize a man-in-the-middle attack or other hacks which may be attempted to gain unauthorized usage of the electronic vaporizer and/or associated housings/cartridges. For example, the controllers in different housings may be able to carry out an SSL protocol to form an encrypted communication channel between the controllers through which certificates, RFID readings, biometric inputs, housing serial numbers, and/or other data may be passed therebetween. Also, it should be understood that embodiments that include an RFID/Bluetooth/NFC reader may be operative to carry out a handshaking protocol with an article. Such a handshaking protocol may establish encrypted communications with the article. The handshaking protocol may also include authentication of the article using digital certificates or other cryptographic processes.

In addition, in the previously described embodiments, the data store 924 and/or 926 may be programmed when manufactured, by a pharmacist, and/or by another authorized user to include usage and dosage information that correspond to the previously described predetermined periods of time and predetermined thresholds used to limit the amount of vaporized solution inhaled by a user. For such embodiments, the controller 912 and/or 928 may include or be in operative connection with a clock that can provide time information usable to control when to enable and/or prevent usage of the electronic vaporizer between the time intervals specified by the dosage information stored in the data store 924 and/or 926.

It should also be appreciated that one or more of the previously described embodiments of the electronic vaporizer may include a communication device for additional or other purposes besides programming the data store 926. For example, an embodiment of the electronic vaporizer may use a communication device to communicate data stored in the data store 924 associated with monitored usage of the device to an external computing device such as a remote server. The computing device may also communicate a unique identifier (e.g., a serial number, user account number, userID) to the remote server. The remote server may compile statistics regarding use of the electronic vaporizer (associated with the unique identifier) for use by a doctor or other person to evaluate and/or monitor its use. Also, the remote server may provide usage and/or dosage data to the electronic vaporizer to activate and/or modify future limits on the operation of the electronic vaporizer. In order to connect to the remote server, the communication device (e.g. a USB port, Bluetooth, NFC, Wireless Ethernet) of the electronic vaporizer may be connected to a corresponding communication device of a mobile phone, PC, or other computing device which has access to the Internet.

In addition, it should be understood that in some embodiments, in which a generator serves as a sensor (to monitor the intake of vaporized solution), the generator may not be used to provide electrical energy to power the heater element. Rather the generator may only correspond to an air flow meter. For example, the generator may be of a size that is adapted for monitoring airflow and may not be capable of timely generating a sufficient amount of energy to power the heater element. In such cases, the electronic vaporizer may include a battery as described in previous embodiments and/or some other type of power source or power harvesting device.

Also, it should be appreciated that one or more of the embodiments described herein may be operative to carry out and/or facilitate analyzing and/or capturing information about the user of the electronic vaporizer. For example in a further embodiment, the electronic vaporizer may include one or more sensors that are operative to analyze breath, saliva, skin, sweat, tissue, and/or cells of the user using the electronic vaporizer. Such sensors may be operative to acquire data from such substances, which data is stored in one or more data stores in the electronic vaporizer. Such data may be downloadable to a remote system (via a wired or wireless connection with the electronic vaporizer) in order for medical conditions and/or other characteristics of the user to be determined and evaluated by the user themselves, caregivers, and/or medical professionals.

Also in a further embodiment, the electronic vaporizer may be operative to acquire and store substances from a user (e.g., breath, saliva, skin, sweat, tissue, and/or cells) in a storage chamber within the electronic vaporizer during use of the electronic vaporize. The electronic vaporizer and/or the storage chamber may then be connected to one or more instruments capable of extracting and analyzing the contents of the storage chamber for medical conditions or other characteristics (e.g., cancer, vitamin deficiencies, drug use).

As discussed previously the power source used in one or more embodiments described herein may correspond to a rechargeable battery. Such a rechargeable battery may be capable of being rapidly charged in a relatively fast time period (e.g., <1 hour, <30 minutes, or other time period that is less than 2 hours to charge a battery from <10% of a full charge to >90% of a full charge). In the embodiment, a rapid charger that is used to rapidly charge a battery in an electronic vaporizer in this described manner, may be capable of being plugged into any other power sources such as an AC outlet, a USB port or a DC power source.

In addition, it should be appreciated that one or more embodiments described herein may include an epinephrine autoinjector or other type of autoinjector that is capable of being used by a user to inject a medication capable of treating an allergic reaction, anaphylactic shock or other condition that requires an injection of a medication into the bloodstream of a user. Such an autoinjector may be included in an additional housing/cartridge removably mountable to one of the other housings/cartridges described herein and/or may be integrated into one of the housings/cartridges described herein. Such an autoinjector may be capable of being activated by placing an end of the housing/cartridge with the autoinjector adjacent a user's body (e.g. a muscle) and pressing a button which causes a spring loaded needle in the autoinjector to enter tissue of the user and inject a medication stored in the housing into the body of the person.

Further, it should be noted that any of the chemical delivery examples described herein (vaporizer, capsule, pellet, autoinjector) may be operative to deliver any type of desirable substance to a user, including but not limited to: medications, antibiotics, pain killers, pharmaceuticals, narcotics, nicotine, tobacco, THC, marijuana, caffeine, vitamins, herbal substances, food, steroids, epinephrine, insulin, and/or any other substances that may be desirable by an end user of the described embodiments. Also, it should be appreciated that that one or more example embodiments may correspond to a cartridge that comprises of a housing, heating element located in the center airflow and a storage mechanism for holding the active and inert ingredients. In addition one or more embodiments may correspond to a cartridge that comprises of a housing, heating element surrounding the center of the airflow for the purpose of vaporization of ingredient or ingredients. Further one or more embodiments may correspond to a heating eliminate that directly or indirectly contacts a solution, solid or powder to be transferred in a gashouses, liquid, powder or solid state either directly or indirectly through a carrier medium of any kind in order to be inhaled through breath or artificial breathing mechanism to be delivered either directly or indirectly to the user or subject. Also, one or more embodiments may correspond to a heating element made from metallic substance such as nichrome, nickel chromium, gaseous heating element, ceramic, ceramic composite, carbon, carbon hybrid, carbon fiber, polymer, hybrid polymer or any other material that are capable of heating a solution, solid or powder to a gashouses state for the purpose of delivering a desired substance or combination of substances in order to deliver flavors, nicotine, medicines, recreational consumables, tobacco, marijuana, vitamins or any other substance or combination of substances for consumption by humans or animals of any kind. In addition one or more embodiments may correspond to a device or group of devices that use software and/or hardware that can also use artificial intelligence to singularly or collectively and can be linked either wirelessly or through other hard connection mechanisms to allow for the devices and user to collaborate or share collective data either knowingly or unknowingly directly or through a medium such as a server, internet or data bank locally or remotely for data collection as well as collaboration.

It is noted that several examples have been provided for purposes of explanation. These examples are not to be construed as limiting the hereto-appended claims. Additionally, it may be recognized that the examples provided herein may be permutated while still falling under the scope of the claims.

What is claimed is:

1. An apparatus comprising:
  a cartridge that facilitates provision of a vaporized solution to an individual, the cartridge comprising:
    a housing that comprises an interior; and
    a heating element located in the interior of the housing, wherein the heating element is configured to vaporize a solution for oral provision to the individual; and
  a power harvesting device operative to acquire energy from an airflow for use with powering the heating element.

2. The apparatus of claim 1, wherein the cartridge further comprises an absorbent material located in the interior of the housing, wherein the absorbent material includes the solution, and wherein the heating element is operative to vaporize the solution that is included in the absorbent material.

3. The apparatus of claim 2, wherein the cartridge includes opposed first and second ends wherein the cartridge includes an airflow passageway that extends through the interior between the first and second ends.

4. The apparatus of claim 3, wherein the cartridge includes a central longitudinal axis between the first end and the second end, wherein the cartridge further comprises a first aperture on the first end and a second aperture on the second end, wherein the airflow passageway extends axially between the first end and the second end along the central longitudinal axis, and wherein the airflow passageway is configured to allow airflow through the cartridge.

5. The apparatus of claim 4, wherein the absorbent material surrounds the airflow passageway in the interior of the housing.

6. The apparatus of claim 4, wherein the heating element comprises a wicking material to attract the solution from the absorbent material to the heating element.

7. The apparatus of claim 4, wherein the solution comprises at least one of nicotine, caffeine, THC, or any combination thereof.

8. The apparatus of claim 1, further comprising a second housing that is operative to releasably connect to the housing of the cartridge, wherein the second housing includes the power harvesting device.

9. The apparatus of claim 8, wherein the housing of the cartridge has a generally cylindrical shape and includes a first end and a second end that is opposite the first end, and wherein the first end comprises a conductive material that is operable to place the heating element in electrical connection with the power harvesting device.

10. The apparatus of claim 9, wherein the second end is at least partially covered by at least one of a paper, wood, a flavored covering, or any combination thereof.

11. The apparatus of claim 9, wherein the second end includes a tip comprised of a malleable polymer.

12. An apparatus comprising:
a cartridge that facilitates provision of a vaporized solution to an individual, the cartridge comprising:
a housing that comprises an interior; and
a heating element located in the interior of the housing, wherein the heating element is configured to vaporize a solution for oral provision to the individual;
a power harvesting device operative to acquire energy from the environment for use with powering the heating element;
at least one controller; and
at least one sensor and a data store in operative connection with the at least one controller, wherein the at least one sensor is operative to detect at least one characteristic of at least one of breath, saliva, sweat, and cells of the individual, wherein the at least one controller is operative to cause data representative of the at least one characteristic to be stored in the data store.

13. An apparatus comprising:
a cartridge that facilitates provision of a vaporized solution to an individual, the cartridge comprising:
a housing that comprises an interior; and
a heating element located in the interior of the housing, wherein the heating element is configured to vaporize a solution for oral provision to the individual; and
a power harvesting device operative to acquire energy from the environment for use with powering the heating element, wherein the power harvesting device includes a generator, wherein air flow through the apparatus is operative to cause the generator to generate electricity usable to power the heating element.

14. The apparatus according to claim 13, further comprising a controller and a data store, wherein the controller is operative responsive at least in part to the generator, to determine an estimate of an amount of vaporized solution inhaled by the individual, and to store data representative of the estimated amount in the data store.

15. The apparatus according to claim 14, wherein the controller is operative to control when to operate the heating element to further vaporize the solution responsive at least in part to the data stored in the data store.

16. The apparatus according to claim 13, further comprising a controller and a reading device, wherein the reading device is operative to acquire data from the individual which is used by the controller to verify that a predetermined individual is adjacent the apparatus prior to causing the heating element to vaporize the solution.

17. The apparatus according to claim 16, wherein the reader device is a biometric reader.

18. The apparatus according to claim 13, further comprising a controller and a reading device, wherein the reading device is operative to wirelessly acquire data from an article adjacent the apparatus, which data is used by the controller to verify that a predetermined article is adjacent the apparatus prior to causing the heating element to vaporize the solution.

19. The apparatus according to claim 18, wherein the article includes at least one of a ring, an item capable of being carried by the individual, or a combination thereof.

20. A method comprising:
with an apparatus including a cartridge that facilitates provision of a vaporized solution to an individual, the cartridge comprising a heating element located in the interior of the housing, wherein the heating element is configured to vaporize a solution for oral provision to the individual, wherein the apparatus includes a power harvesting device operative to acquire energy from the environment for use with powering the heating element,
a) receiving an airflow through the housing;
b) through operation of the power harvesting device, generating electricity responsive to the airflow in (a); and
c) using the electricity generated in (b) to cause the heating element to vaporize the solution.

21. An apparatus comprising:
a cartridge that facilitates provision of a vaporized solution to an individual, the cartridge comprising:
a housing that comprises an interior, wherein the housing is configured to enable an airflow through the interior of the housing; and
a heating element located in the interior of the housing, wherein the heating element is configured to vaporize a solution for oral provision to the individual; and
a power harvesting device operative to generate electrical energy responsive to the airflow, wherein the heating element is operative to use the electrical energy generated by the power harvesting device to vaporize the solution.

* * * * *